United States Patent [19]
Gabrovsek

[11] Patent Number: 5,692,532
[45] Date of Patent: Dec. 2, 1997

[54] TWO-PIECE DENTAL FLOSSING DEVICE

[76] Inventor: Peter V. Gabrovsek, 6660 Dewey Rd., Thompson, Ohio 44086

[21] Appl. No.: 671,139

[22] Filed: Jun. 27, 1996

[51] Int. Cl.⁶ ........................................... A61C 15/00
[52] U.S. Cl. ........................................ 132/325; 132/323
[58] Field of Search ............................ 132/323, 324, 132/325, 326, 327

[56] References Cited

U.S. PATENT DOCUMENTS

| | | |
|---|---|---|
| 911,068 | 2/1909 | Perkins. |
| 1,174,016 | 2/1916 | Kenyon. |
| 1,465,669 | 8/1923 | Hochstadter. |
| 1,733,631 | 10/1929 | Spiegel et al.. |
| 1,966,463 | 7/1934 | Rose. |
| 2,644,469 | 7/1953 | Cohen. |
| 4,162,688 | 7/1979 | Tarrson et al.. |
| 4,574,823 | 3/1986 | Uriss. |
| 4,655,234 | 4/1987 | Bowden. |
| 4,790,336 | 12/1988 | Kuo. |
| 4,898,196 | 2/1990 | Eason. |
| 5,301,698 | 4/1994 | Ballard ........................ 132/325 |
| 5,375,614 | 12/1994 | Navratil ....................... 132/325 |
| 5,423,338 | 6/1995 | Hodge et al. ................. 132/325 |

Primary Examiner—Nicholas D. Lucchesi
Attorney, Agent, or Firm—Watts, Hoffmann, Fisher & Heinke Co. LPA

[57] ABSTRACT

A two-piece dental flossing device is disclosed. The device includes a floss dispensing member and a floss wrapping member which is detachable from the floss dispensing member. The floss dispensing member comprises a body portion with a generally cylindrical throughbore adapted to hold a floss dispensing assembly including a spool of dental floss. The spool is rotated within the throughbore to release floss which extends through a channel in a stem of the floss dispensing member extending from the body portion. The two members allow for two-handed flossing and function as extensions of the fingers facilitating the flowing process.

4 Claims, 5 Drawing Sheets

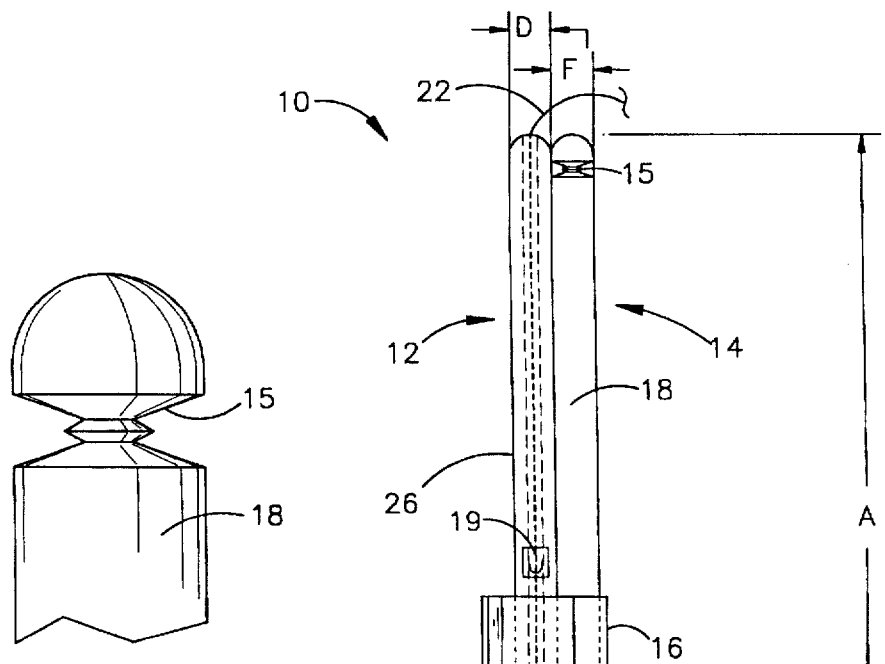
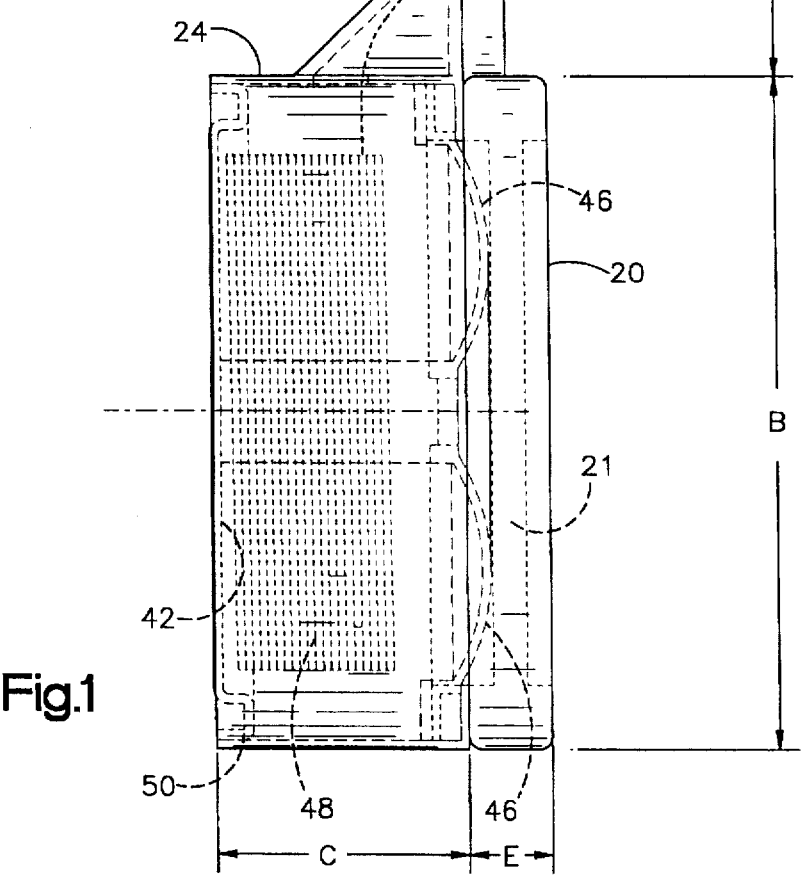
Fig.1A
Fig.1

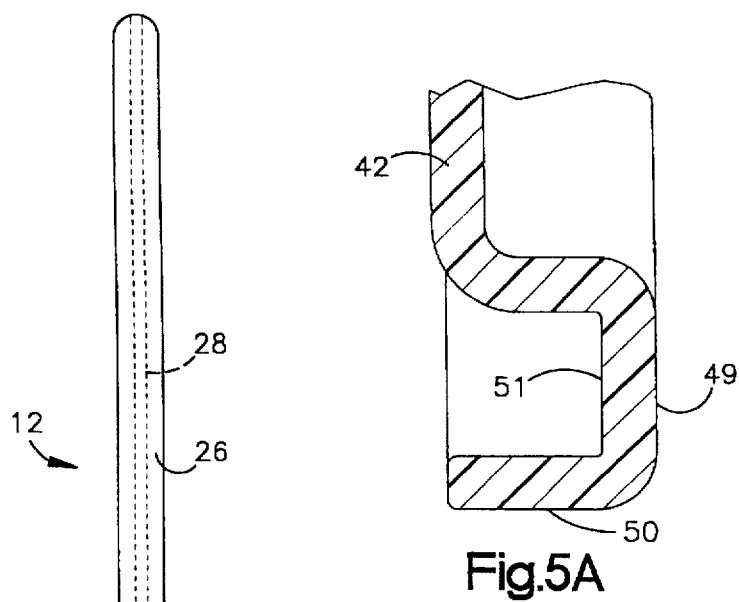
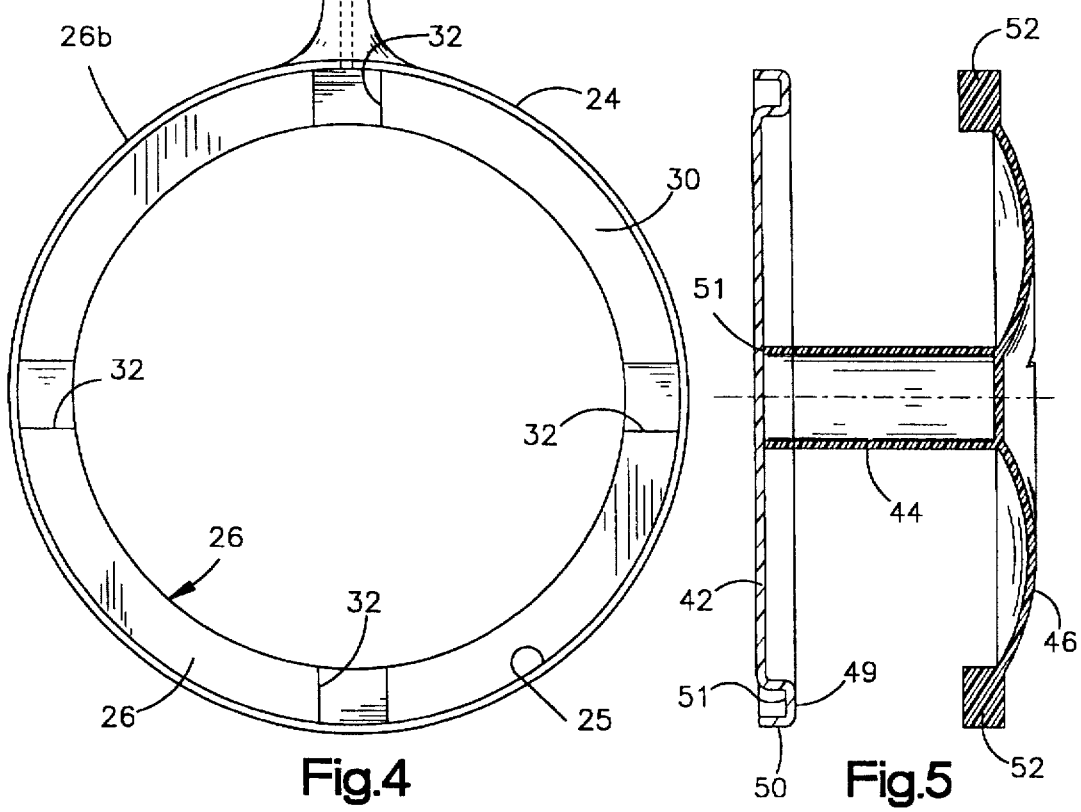

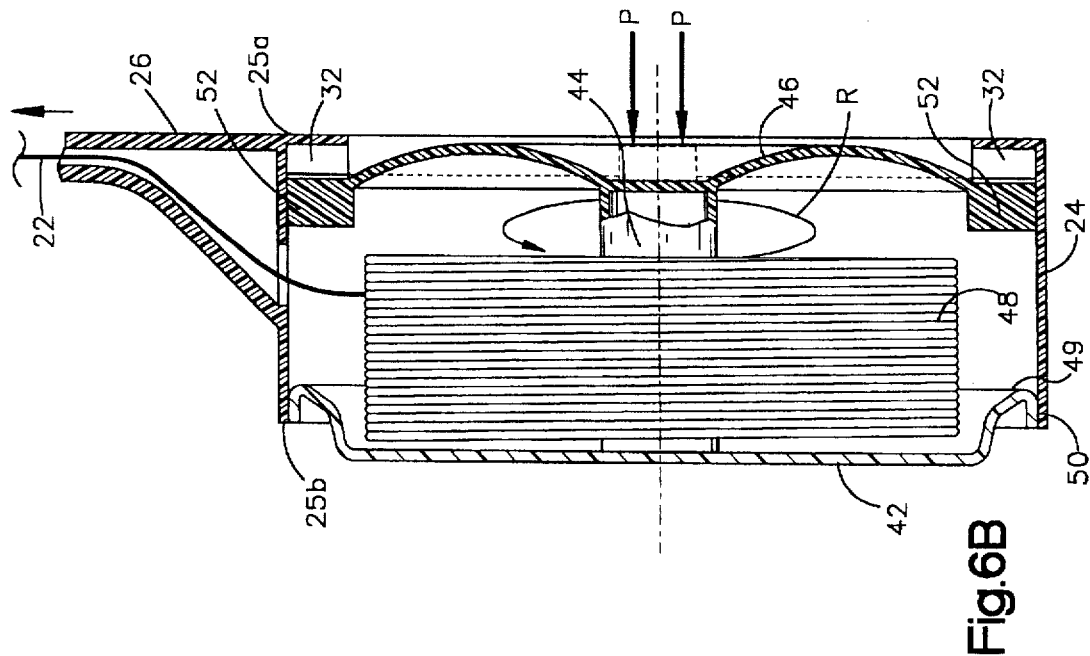
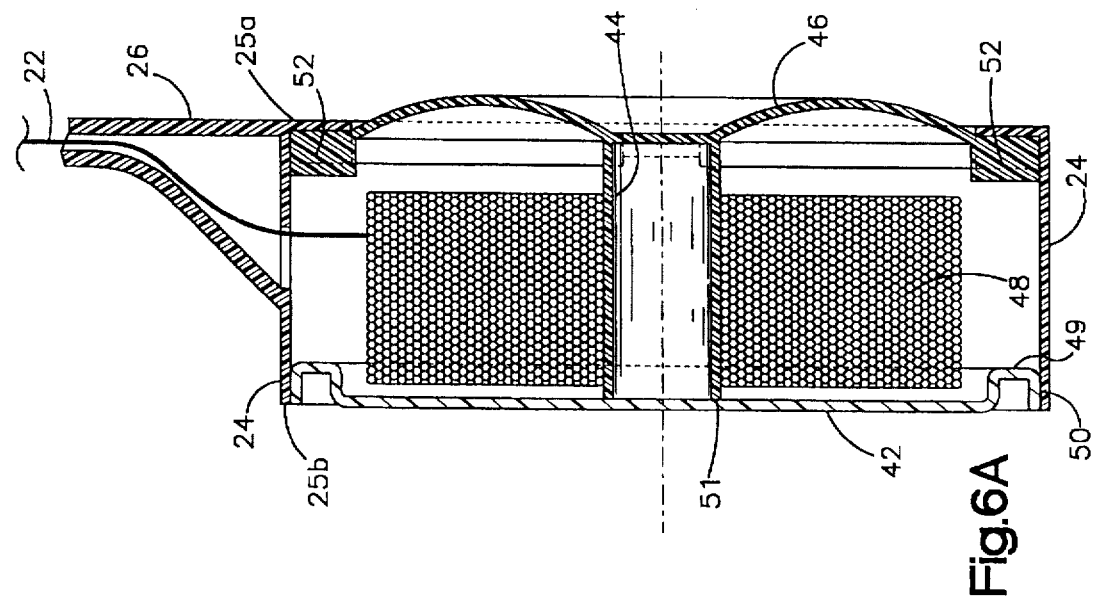

5,692,532

1

TWO-PIECE DENTAL FLOSSING DEVICE

FIELD OF INVENTION

This invention is related generally to dental flossing devices and, more particularly, to a two piece dental flossing device.

DESCRIPTION OF RELATED ART

Dental flossing has long been recognized as an effective means for removing food between teeth that normal brushing is unable to reach. In addition, flossing aids in reducing plaque buildup on teeth and in preventing various gum diseases. The most common method of flossing involves wrapping a strand of dental floss around the index finger of each hand. The fingers, with a section of floss suspended between them, are inserted into the mouth cavity and the fingers are appropriately moved to cause the suspended section of floss to enter the space between adjacent teeth and manipulate the floss against the tooth surfaces.

The disadvantages of this by-hand flossing method are two-fold. First, the floss wrapped around the finger tends to cut into the skin thereby causing pain to the flosser. Second, the size of the flossers fingers may make it difficult, if not impossible, to insert and manipulate the floss between his teeth, especially those teeth located toward the back potion of the mouth cavity.

Several attempts have been made to improve upon the two-handed finger method of flossing by providing a device which enables the user to easily floss the back teeth and which does not cut into the users fingers. Flossing devices developed to date may be characterized as unitary structures which have a fixed length gap at or near the distal end of the device across which a section of floss is tautly suspended. The user manipulates the shaft of the device with one hand to cause the suspended floss to enter the space between adjacent teeth and be properly manipulated against the tooth surfaces. See, for example, one-handed flossing devices disclosed in U.S. Pat. Nos. 911,068, 1,465,669, 1733,631, 1,966,463, 4,644,469, 4,655,234, 4,574,823, 4,790,336 and 4,898,196.

However, the one-handed devices have a serious drawback in comparison to the two-handed finger method of flossing in that the floss cannot easily be controlled and manipulated. Simply put, two hands working in synchronization allow for greater control of the position and movement of the floss than can be achieved with one hand performing the same task. What is needed is a two piece dental flossing device, one piece adapted to be held in each hand of the user, allowing for greater control by the user in the insertion and manipulation of the floss between adjacent teeth.

SUMMARY OF THE INVENTION

The two piece dental flossing device of the present invention comprises a dental floss dispensing member and a dental floss wrapping member which is detachable from the floss dispensing member. The floss wrapping member includes a body potion and an extending stem. The stem includes a w-shaped notch near a distal end. The dental floss dispensing member comprises a body portion with a generally cylindrical throughbore adapted to rotatably hold a floss dispensing assembly including a spool of dental floss. The dental floss dispensing member further includes a stem extending from the body portion and having a longitudinal channel in communication with the cylindrical throughbore.

2

The floss dispensing assembly includes an axle supporting the spool of floss and a hub affixed to one end of the axle. The opposite end of the axle abuts a plastic retaining cap which is affixed to the floss dispensing member body portion to secure the floss dispensing assembly in the cylindrical throughbore. The hub includes locking hubs extending radially outwardly from an outer periphery of the hub. In a locked position of the floss dispenser assembly, the locking hubs are held stationary in openings in an annular rim at one end of the body portion. Floss from the spool of floss extends through the channel and exits the dispensing member near a distal end of the stem.

When the user desires to dispense a section of dental floss for flossing, the hub is pressed inwardly, the retaining cover flexes sufficiently to permit the locking hubs to move out of engagement with the annular rim openings thereby permitting the floss dispensing assembly to rotate within the floss dispensing member body portion throughbore.

To use the device, the floss wrapping member is detached from the floss dispensing member and an end portion of the floss is wrapped around the w-shaped notch portion of the floss wrapping member, the "w" shape of the notch causes the floss to cross wrap on itself as the floss is wrapped around the notch thereby causing the floss to be securely wrapped with no slippage. The user then presses the hub inwardly and pulls the wrapping member in a direction away from the dispensing member until a desired length of floss bridges the two members.

An object of this invention is to provide a two piece dental flossing device, one piece adapted to be held in each hand of the user, thereby allowing for greater control by the user in the insertion and manipulation of the floss between adjacent teeth. Another object of this invention is to provide a two piece dental flossing device which allows a user of the device to easily dispense a section of floss for flossing and has a locking mechanism to prevent any additional undesired dispensing of floss. Another object of the invention is to provide a two piece dental flossing device having extending stem portions, the distal portions of which support a dispensed section of floss and which may easily be manipulated and function as extensions of the user's fingers in flossing with the dispensed floss section. Yet another object of this invention is to provide a two piece dental flossing device that allows the user to easily reach all of his or her teeth with the dispensed section of floss including those teeth located toward the back of the mouth cavity.

The aforementioned and other aspects of the present invention are described in more detail in the detailed description and accompanying drawings which follow.

BRIEF DESCRIPTIONS OF DRAWINGS

FIG. 1 is a side elevation view of the two piece dental flossing device of the present invention;

FIG. 1A is a side elevation view of an upper portion of a dental floss wrapping member of the dental flossing device of FIG. 1;

FIG. 4 is a front elevation view of the dental floss dispensing member with the floss dispensing assembly removed;

FIG. 5 is a sectional view of the floss dispensing assembly and a retaining cap with a spool of floss removed from the assembly;

FIG. 5A is an enlarged section view of an end portion of the retaining cap of FIG. 5;

FIG. 6A is a view, partly is side elevation and partly in section, of a body portion of the dental floss dispensing member with the floss dispensing assembly in a locked position; and FIG. 6B is a view of the body potion of the dental floss dispensing member of FIG. 6A with the floss dispensing assembly in an unlocked or floss dispensing position.

DESCRIPTION OF THE PREFERRED EMBODIMENT

Figure 2:
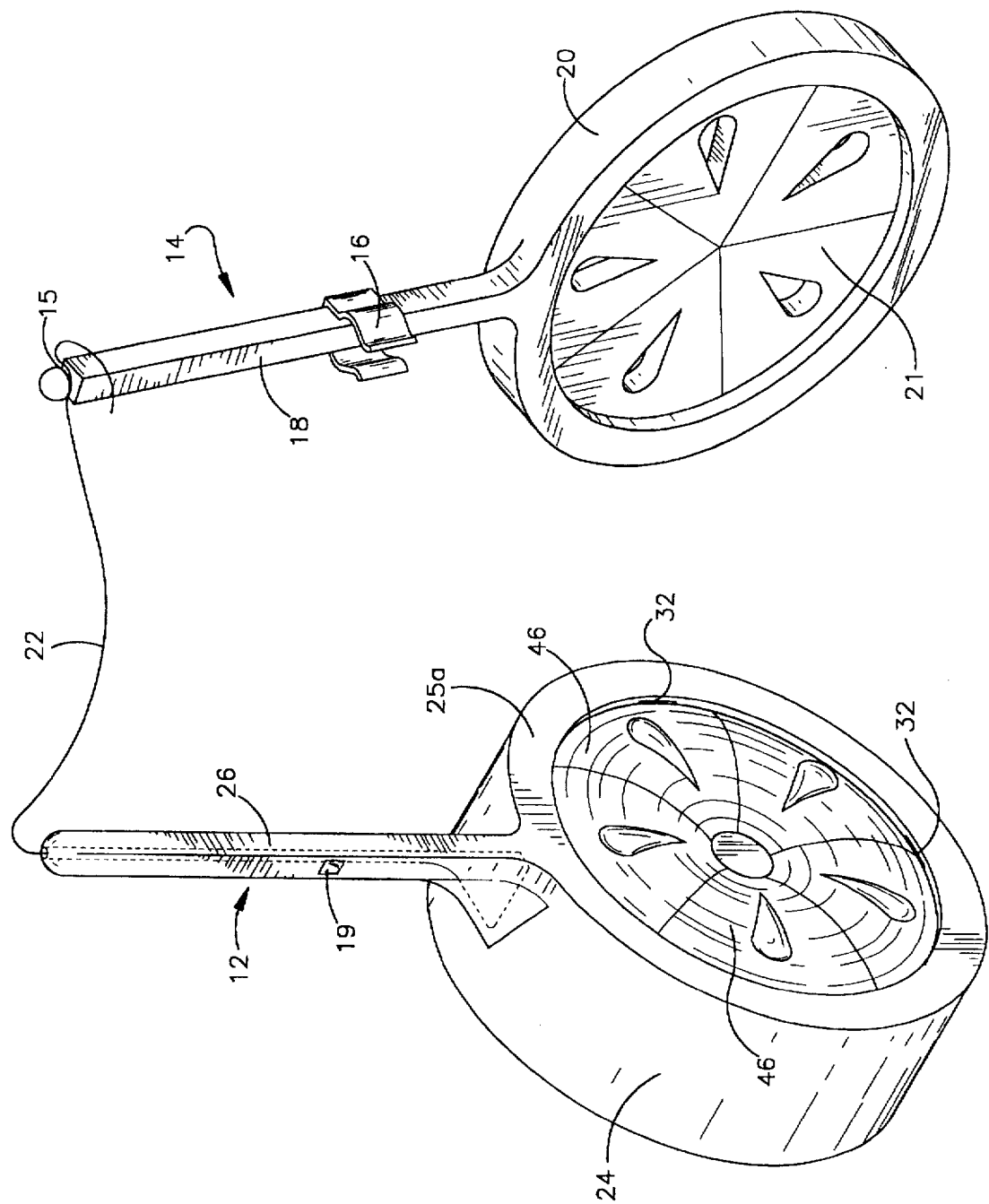
FIG. 2 is a perspective view of the dental flossing device of FIG. 1 with a dental floss dispensing member separated from the dental floss wrapping member and a dispensed section of floss bridging the dispensing member and the wrapping member as the device would be in use.

The two piece dental flossing device of the present invention is shown generally at 10 in FIG. 1. The device 10 comprises two pieces or members, a dental floss dispensing member 12 and a dental floss wrapping member 14. A clip 16 is affixed to a stem 18 of the floss wrapping member 14. The clip 16 snaps onto a stem 26 of the floss dispensing member 12 and functions to releasably attach the floss wrapping member 14 and the floss dispensing member 12 when the device 10 is not in use. The floss dispensing member 12 and the floss wrapping member 14 may be fabricated from plastic or any suitable material which is lightweight, strong and inexpensive. The dispensing member 12 includes a floss cutter 19 affixed to a lower portion of the dispensing member stem 26. The cutter 19 may comprise a small piece of metal with a center portion stamped out to a form a v-shaped cutting surface at the vertex of the stamped center portion and the remaining flat metal.

FIG. 2 illustrates the device 10 in a position in which it would be used. The floss dispensing member 12 and the floss wrapping member 14 are separated and a section of floss 22 bridges the two members 12, 14. As can best be seen in FIG. 1A, the floss wrapping member 14 includes a "w" shaped notch 15 near a distal end of the stem 18. An end potion of the floss 22 extending from a stem 26 of the dispensing member 12 is wrapped around the notch 15. The shape of the notch results in cross wrapping of a portion of the floss 22 wrapped around the notch. The cross wrapping of the floss around the notch 15 provides for a secure wrapping of the floss 22 on the floss wrapping member 14. The floss wrapped around the notch will not unravel, slip or pull free as the device 10 is used to floss the user's teeth.

The floss wrapping member 14 includes a cylindrical body portion 20 extending from the stem portion 18. A thin disk 21 is disposed within a throughbore defined by the body portion 20. The floss wrapping member 14 is sized to be comfortably grasped by one hand of a user. The body portion 20 of the floss wrapping member 14 is cradled within a palm of the user's hand and the user's thumb, index and middle fingers extend a portion of the way up the stem 18. Similarly, the floss dispensing member 12 includes a body portion 24 with the stem 26 extending therefrom. The floss dispensing member 12 is sized to be comfortably grasped by the other hand of the user with the body portion 24 cradled within a pair of the user's hand and the user's thumb, index and middle fingers extending a portion of the way up the stem. When the floss dispensing and floss wrapping members 12, 14 are grasped as described, precise manipulation of the floss section 22 within the user's mouth and between the user's teeth is facilitated. In essence, the stems 26, 18 function as extensions of the user's fingers and permit precise manipulation of the floss section 22. Moreover, the stems 26, 18 provide sufficient length to permit the user to easily floss hard to reach back teeth.

With reference to FIG. 1, suitable dimensions for the device 10 are as follows:

A=2¼"
B=2"
C=¾"
D=⅛"
E=¼"
F=⅛"

The floss dispensing member body portion 24 includes a cylindrical throughbore 25 (FIGS. 3 and 4) extending between opposite ends 25a, 25b (FIGS. 6A and 6B) of the floss dispensing member 12. Extending inwardly into the throughbore 25 from one end 25a of the body portion 24 is a narrow rim 26, as can best be seen in FIG. 4, spaced evenly around the rim are four notches 32 cut into an inwardly facing surface 30 (FIG. 4) of the rim 26. The notches 32 function as part of a locking mechanism to be described below. A floss dispensing assembly 40 rotatably fits with the throughbore 25 of the body portion 24.

Figure 3:
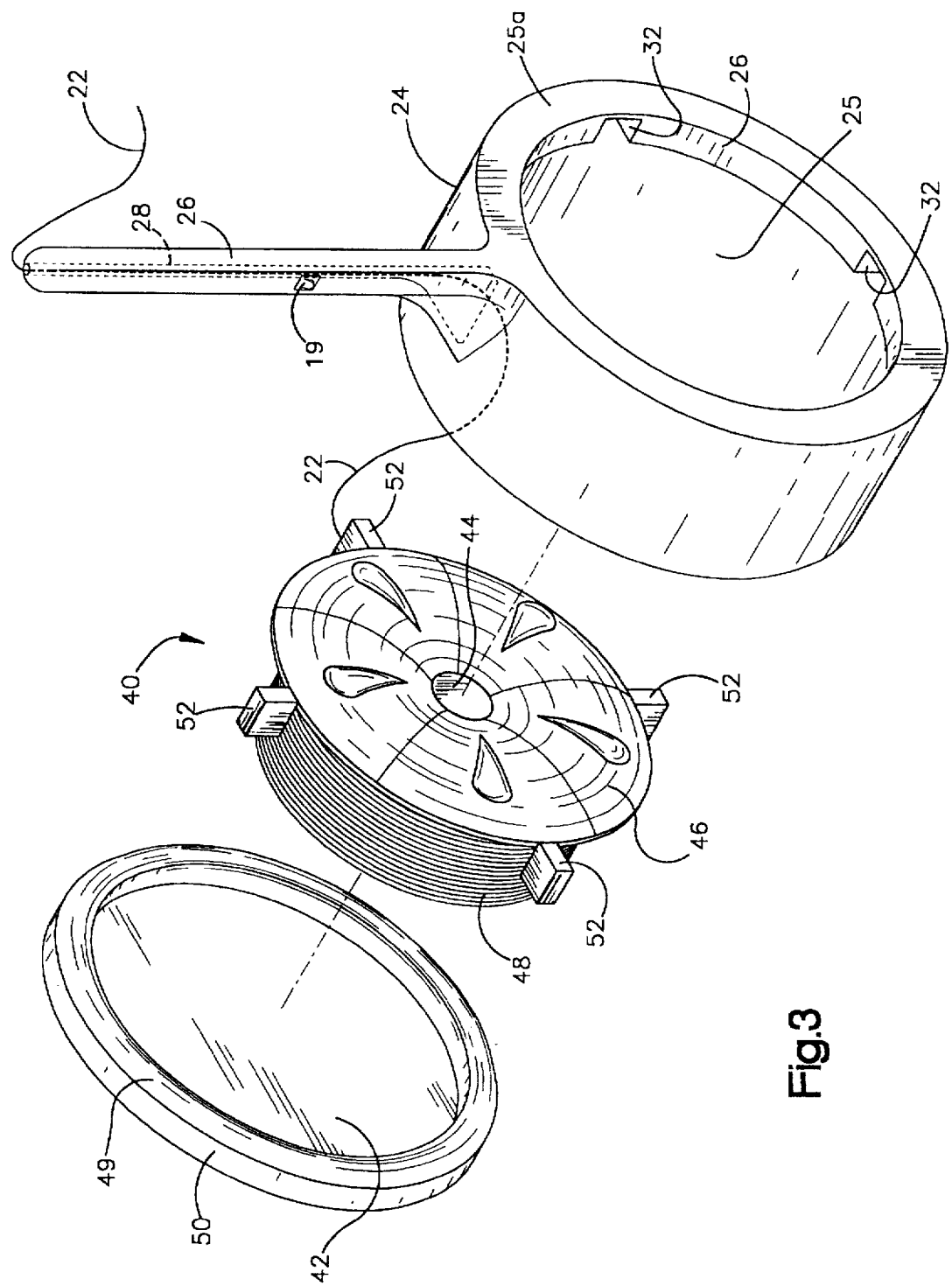
FIG. 3 is a exploded view of the dental floss dispensing member including a dental floss dispensing assembly.

The floss dispensing assembly 40 includes a spool of dental floss 48, a plastic axle 44 supporting the spool of dental floss and a bowed plastic hub 46 extending from one end of the axle, as can best be seen in FIG. 6A. The hub 46 and axle 44 may be one integral piece as shown in FIGS. 6A and 6B or may be separate pieces affixed together with adhesive or another suitable means. As can be seen in FIG. 3, the floss 22 extends from the spool of floss 48 and is threaded through a longitudinal channel 28 through the floss dispensing member stem 26 and exits a distal end of the stem where it is available to be wrapped around the notch 15 of the floss wrapping member and/or cut by the cutter 19.

A retaining cap 42, comprised of a flexible, resiliently deformable piece of plastic, secures the floss dispensing assembly 40, in place within the body portion throughbore 25. As can best be seen in FIG. 5A, an outer rim 49 of the retaining cap 42 is "c" shaped. An outer periphery 50 of the outer rim 49 is secured to an inner periphery of the body portion 24 defining the throughbore 25. Specifically, the outer periphery 50 is secured to a portion of the inner periphery of the body potion 24 adjacent the end 25b of the body potion. The retaining cap 42 may be secured to the body portion inner periphery with adhesive, ultrasonic welding or any other suitable method. An end 51 of the axle 44 abuts a central portion of the retaining cap 42. Preferably, a central portion of the retaining cap 42 is stiffer than the outer rim 49.

The locking mechanism of the floss dispensing member 12 will now be explained. The locking mechanism includes the four locking hubs 52, the four notches of the annular rim 26 and the retaining cap 42. When the retaining cap 42 in an undeflected position (FIG. 6A), it biases the four locking nubs 52 against the inwardly facing surface 30 (FIG. 4) of the rim 26. The four hubs 52 are evenly spaced about the periphery of the hub 46 and are sized to fit in the notches 32. If the nubs 52 are not in the notches 32, when the floss 22 is pulled, the axle 44 and hub 46 will rotate a portion of turn until the nubs and notches are aligned at which point the nubs will drop into the notches and prevent the axle and hub from rotating any further. When the nubs 52 are within the notches 32, as seen in FIG. 6A, the axle 44 and hub 46 are prevented from rotating and no floss is dispensed from the spool of floss 48. This is referred to as the locked position.

To move the hubs 52 from a locked position to an unlocked or floss dispensing position, the user presses a central portion of the hub 46 inwardly in the direction shown by the arrows labeled P in FIG. 6B with a thumb or finger of the hand holding the floss dispensing device 12. Since the retaining cap 42 is resiliently deformable, a slight pressure on the central potion of the hub 46 will cause the outer rim 49 of the cap 42 to deflect outwardly (that is, in the direction pointed to by the arrows labeled P) while still remaining attached to the inner periphery of the body portion 24. The c shaped outer rim 49 of the cap 42 deflects as shown in FIG. 6B permitting the axle 44 and hub 46 to move laterally in the direction pointed to by the arrows labeled P.

The central portion of the retaining cap 42, being stiffer than the outer rim 49, does not deflect as much as the outer rim. Thus, a slight clearance space is maintained between the spool of floss 48 and the inner face of the retaining cap even when the cap is deflected outwardly (FIG. 6B). The clearance space avoids extra friction between the spool of 48 which rotates with respect to the stationary cap 42 as the floss 22 is pulled from the floss dispensing assembly 40. However, it should be appreciated that even if the retaining cap central portion is more flexible than shown in FIG. 6B and contacts the spool of floss 48 when the cap 42 is deflected, the floss 22 will still be appropriately dispensed, that is, the fictional force between the spool of floss and the cap will not be so great as to prevent the spool from rotating with respect to the cap when the floss 22 outside the stem 26 is pulled in a direction away from the floss dispensing member 12.

As the axle 44 and hub 46 move laterally, the locking nubs 52 moves laterally out of engagement with the notches 32 as shown in FIG. 6B. As the hub 46 is pressed, the user pulls on the floss 22 in a direction away from the floss dispensing member 12. As soon as the locking hubs 52 disengage the notches 32, the axle 44 and hub 46 will rotate as shown by the arrow labeled R within the throughbore 25 because of the force applied by the user in pulling on the floss 22 and floss will be dispensed from the spool of floss 48 through the channel 28. After a desired length of floss is dispensed, the user releases pressure on the hub 46 and pulls on the floss a fraction of a turn until the locking hubs 52 engage the notches 32 and the floss dispensing assembly is again in the locked position.

To use the device 10, the user separates the two members 12, 14. An end portion of the floss 22 extending from the floss dispensing member 12 (remaining after the floss was cut off on the floss cutter 19 after the previous use of the device) is wrapped around the floss wrapping member notch 15. After wrapping a sufficient portion of floss around the notch 15 to prevent the floss from sliding off the notch 15 during use, the user depresses the hub 46 of the floss dispensing member 12 with a finger or thumb of one hand to release the locking mechanism and simultaneously pulls the floss wrapping member 14 held in the other hand in a direction away from the floss dispensing member. Floss will be pulled out from the spool of floss 48 as the floss wrapping member 14 is moved away from the floss dispensing member 12. When a desired length of floss bridges the two members 12, 14, the hub 46 is released and the floss wrapping member 14 is pulled a very short additional distance away from the floss dispensing member 12 until the locking mechanism returns to the locked position.

After use of the dispensed floss section 22 by the user to floss his or her teeth, the portion of the floss wrapped around the notch 15 is unwrapped from the notch and the used floss is cut off using the cutter 19. If a new section of floss is desired during flossing, the above described method of wrapping and dispensing may be repeated. Furthermore, if desired, a short additional amount of floss may be dispensed via the method described above before cutting the used floss off to make sure that the floss extending from the stem 26 is clean, unused floss since this floss will be used as the notch wrapping floss in the next use of the device 10. After flossing is complete, the members 12, 14 are then clipped together using the clip 16 and the device 10 is put away. The device 10 is disposable and is discarded when the spool of floss 48 is exhausted.

The present invention has been described with a degree of particularity, but it is the intent that the invention include all modifications from the disclosed preferred design failing within the spirit or scope of the appended claims.

I claim:
1. A dental flossing device comprising:
   a) a dental floss dispensing member having a body portion and a stem extending therefrom, the body portion defining a throughbore extending between a first end and a second end of the body portion and having a rim adjacent the first end, the rim including an opening facing the second end, the stem including a channel extending from the throughbore through a distal end of the stem;
   b) a floss dispensing assembly including an axle with a first and second end supporting a spool of floss and a hub extending from the first end of the spool, the hub at least partially extending into the rim opening and engaging the rim to prevent the floss dispensing assembly from rotating within the throughbore, floss from the spool of floss threaded through the stem channel;
   c) a flexibly resilient retaining cap affixed to the body portion adjacent the second end of the body portion for maintaining the floss dispensing assembly in the throughbore, the second end of the axle adjacent the cap;
   d) the hub being depressible to disengage the hub from the rim to permit the floss dispensing assembly to rotate within the throughbore and dispense floss through the stem channel, the retaining cap biasing the hub to at least partially extend into the rim opening; and
   e) a floss wrapping member having a notch around which floss dispensed through the stem channel is wrapped, a section of floss extending between the floss wrapping member and the floss dispensing member.

2. The device of claim 1 wherein a floss cutter is affixed to the stem of the floss dispensing member.

3. The device of claim 1 further including a clip to releasably secure the floss dispensing member to the floss wrapping member.

4. The device of claim 1 wherein the floss wrapping member includes a body portion and a stem portion extending therefrom and the notch is disposed near a distal end of the stem portion.

* * * * *